(12) United States Patent
Ranpura et al.

(10) Patent No.: US 9,125,640 B2
(45) Date of Patent: Sep. 8, 2015

(54) BIOPSY DEVICE HAVING A RATCHET DRIVE MECHANISM FOR DRIVING A BIOPSY PROBE ASSEMBLY

(75) Inventors: Himanshu Mahesh Ranpura, Laveen, AZ (US); Chad Van Liere, Tempe, AZ (US)

(73) Assignee: C. R. Bard, Inc., Murray Hill, NJ (US)

( * ) Notice: Subject to any disclaimer, the term of this patent is extended or adjusted under 35 U.S.C. 154(b) by 1017 days.

(21) Appl. No.: 12/981,597

(22) Filed: Dec. 30, 2010

(65) Prior Publication Data

US 2012/0172752 A1 Jul. 5, 2012

(51) Int. Cl.
- A61B 10/00 (2006.01)
- A61B 10/02 (2006.01)

(52) U.S. Cl.
CPC ......... *A61B 10/0275* (2013.01); *A61B 10/0283* (2013.01); *A61B 2010/0208* (2013.01)

(58) Field of Classification Search
CPC .............................................. A61B 2010/0208
USPC .................................................. 600/562–568
See application file for complete search history.

(56) References Cited

U.S. PATENT DOCUMENTS

| | | | |
|---|---|---|---|
| 3,844,272 A | 10/1974 | Banko | |
| 5,526,822 A | 6/1996 | Burbank et al. | |
| 5,928,164 A | 7/1999 | Burbank et al. | |
| 7,276,032 B2 | 10/2007 | Hibner | |
| 7,575,556 B2 | 8/2009 | Speeg et al. | |
| 2006/0258955 A1 | 11/2006 | Hoffman et al. | |
| 2007/0239067 A1 | 10/2007 | Hibner et al. | |
| 2008/0004545 A1 | 1/2008 | Garrison | |
| 2008/0200836 A1 | 8/2008 | Speeg et al. | |
| 2008/0214955 A1 | 9/2008 | Speeg et al. | |
| 2008/0221480 A1 | 9/2008 | Hibner et al. | |
| 2008/0228103 A1 | 9/2008 | Ritchie et al. | |
| 2008/0319341 A1 | 12/2008 | Taylor et al. | |
| 2009/0131816 A1 | 5/2009 | Ritchie et al. | |
| 2009/0131817 A1 | 5/2009 | Speeg et al. | |
| 2009/0131818 A1 | 5/2009 | Speeg et al. | |
| 2009/0131819 A1 | 5/2009 | Ritchie et al. | |
| 2009/0131820 A1 | 5/2009 | Speeg et al. | |
| 2009/0131821 A1 | 5/2009 | Speeg et al. | |
| 2009/0131822 A1 | 5/2009 | Hibner et al. | |
| 2009/0131823 A1 | 5/2009 | Andreyko et al. | |
| 2009/0131824 A1 | 5/2009 | Andrisek et al. | |
| 2009/0227893 A1 | 9/2009 | Coonahan et al. | |
| 2009/0318832 A1 | 12/2009 | Andreyko et al. | |
| 2010/0152610 A1* | 6/2010 | Parihar et al. | 600/566 |
| 2010/0152611 A1 | 6/2010 | Parihar et al. | |
| 2010/0160816 A1 | 6/2010 | Parihar et al. | |
| 2010/0312140 A1 | 12/2010 | Smith et al. | |

FOREIGN PATENT DOCUMENTS

WO 2010107424 A1 9/2010

* cited by examiner

*Primary Examiner* — Brian Szmal
*Assistant Examiner* — H. Q. Nguyen (57) ABSTRACT

A biopsy device includes a first cannula having a first aperture, a second cannula having a second aperture, and a driver unit. The second cannula is disposed co-axially with the first cannula. At least one of the first aperture and the second aperture has a cutting edge. The driver unit has a ratchet drive mechanism operatively coupled to the first cannula and the second cannula. The ratchet drive mechanism includes a first gear fixedly attached to the first cannula. A second gear is fixedly attached to the second cannula. A torsion spring has a first end portion connected to the first gear and a second end portion connected to the second gear. The torsion spring stores energy which when released drivably rotates one of the first gear and the second gear relative to the other of the first gear and the second gear.

12 Claims, 9 Drawing Sheets

BIOPSY DEVICE HAVING A RATCHET DRIVE MECHANISM FOR DRIVING A BIOPSY PROBE ASSEMBLY

CROSS-REFERENCE TO RELATED APPLICATIONS

This is related to PCT/US2009/037289.

MICROFICHE APPENDIX

None.

GOVERNMENT RIGHTS IN PATENT

None.

BACKGROUND OF THE INVENTION

1. Field of the Invention

The present invention relates to medical devices, and, more particularly, to a biopsy device having a ratchet drive mechanism for driving a biopsy probe assembly.

2. Description of the Related Art

A typical biopsy device includes a biopsy driver to which there is mounted a biopsy probe assembly. The biopsy driver typically is configured to be reusable, whereas the biopsy probe assembly is configured to be disposable. The biopsy driver provides the electromechanical power used to drive the biopsy probe assembly. Typically, the biopsy probe assembly has a cannula configured with a sample notch and a tissue sample chamber, and has a tissue cutting mechanism associated with the cannula. During a biopsy procedure, vacuum assistance may be used to help draw tissue through the sample notch and into the sample chamber and maximize the amount of tissue obtained with each sample. Some biopsy devices, commonly referred to as single insertion, multiple samples, or SIMS devices, utilize sample acquisition and delivery mechanisms that allow multiple samples to be acquired from a given lesion region without removing and reinserting the needle after each sample. One type of cutting mechanism used in a vacuum assisted SIMS biopsy device uses rotational and linear motion of a cutter with respect to the sample notch to sever the tissue drawn through the sample notch into the tissue sample chamber. Vacuum is applied to transport the tissue from the tissue sample chamber of the cannula to a sample collection basket. This process may be repeated until the desired amount of tissue has been obtained.

Also, such a typical biopsy device utilizes a biopsy driver having electrical power in the form of a rechargeable battery to facilitate motor driven linear and rotational movement of the cannula and/or the tissue cutting mechanism of the biopsy probe assembly. Such use of motor driven components to drive the cannula and/or the tissue cutting mechanism in the biopsy driver adds cost to the overall biopsy device.

It would be desirable to reduce the cost of the biopsy device without sacrificing the ability to consistently collect high quality tissue samples.

SUMMARY OF THE INVENTION

The present invention provides a biopsy device having a ratchet drive mechanism that stores energy for driving a cutting component of a biopsy probe assembly to harvest a tissue sample during a biopsy procedure.

The invention, in one form thereof, is directed to a biopsy device. The biopsy device includes a first cannula, a second cannula and a driver unit. The first cannula has a first side wall defining a first lumen. The first cannula has a first proximal end and a first distal end. The first cannula has a first aperture extending through the first side wall to the first lumen proximal to the first distal end. The first cannula has a longitudinal axis. A second cannula has a second side wall defining a second lumen. The second cannula has a second proximal end and a second distal end. The second cannula has a second aperture extending through the second side wall to the second lumen proximal to the second distal end. The second cannula is disposed co-axially with the first cannula. At least one of the first aperture and the second aperture has a cutting edge. The driver unit has a ratchet drive mechanism operatively coupled to the first cannula and the second cannula. The ratchet drive mechanism includes a first gear, a second gear and a torsion spring. The first gear is fixedly attached to the first cannula. The second gear is fixedly attached to the second cannula. The torsion spring is located between the first gear and the second gear. The torsion spring has a first end portion and a second end portion. The first end portion is connected to the first gear and the second end portion is connected to the second gear. The ratchet drive mechanism is configured such that the torsion spring stores energy which when released drivably rotates one of the first gear and the second gear relative to the other of the first gear and the second gear.

The invention, another form thereof, is directed to a biopsy device that includes an outer cannula having a first side wall defining a first lumen. The outer cannula has a first aperture extending through the first side wall to the first lumen. The outer cannula has a longitudinal axis. An inner cannula has a second side wall defining a second lumen. The inner cannula has a second aperture extending through the second side wall to the second lumen. The inner cannula is disposed co-axially with the outer cannula in the first lumen. At least one of the first aperture and the second aperture has a cutting edge. A ratchet drive mechanism is operatively coupled to the outer cannula and the inner cannula. The ratchet drive mechanism includes a first gear fixedly attached to the outer cannula. A second gear is fixedly attached to the inner cannula. A torsion spring is located between the first gear and the second gear. The torsion spring has a first end portion and a second end portion. The first end portion is connected to the first gear and the second end portion is connected to the second gear. An outer cannula advance actuator is configured to rotate the first gear in a clocking manner in a first rotational direction. An inner cannula advance actuator is configured to rotate the second gear in a clocking manner in a second rotational direction opposite to the first rotational direction. An outer cannula slide actuator has a first cantilever pawl. The outer cannula slide actuator is configured to selective engage the first gear, wherein when the first cantilever pawl is engaged with the first gear, the first gear and the outer cannula are prevented from rotation in the second rotational direction. An inner cannula slide actuator has a second cantilever pawl. The inner cannula slide actuator is configured to selective engage the second gear, wherein when the second cantilever pawl is engaged with the second gear, the second gear and the inner cannula are prevented from rotation in the first rotational direction.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplifications set out herein illustrate an embodiment of the invention, and such exemplifications are not to be construed as limiting the scope of the invention in any manner.

DETAILED DESCRIPTION OF THE INVENTION

Figure 1:
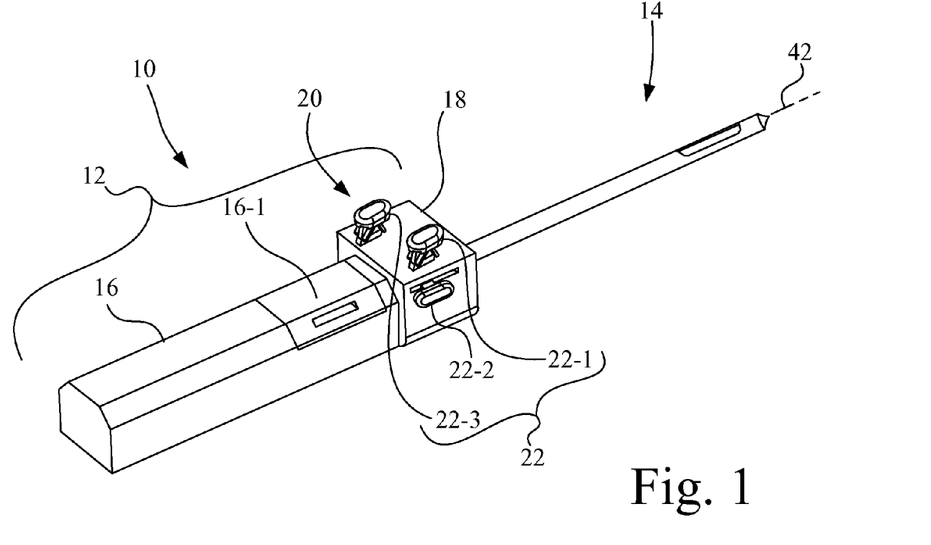
FIG. 1 is a perspective view of a biopsy device including a driver unit and a probe assembly, configured in accordance with an embodiment of the present invention.

Referring now to the drawings and particularly to FIG. 1, there is shown a biopsy device 10 configured in accordance with an embodiment of the present invention. Biopsy device 10 includes a driver unit 12 and a biopsy probe assembly 14.

Driver unit 12 includes a primary housing 16 and a drive housing 18. Primary housing 16 serves as a handle that is grasped by the hand of a user.

In the present embodiment, biopsy probe assembly 14 is permanently mounted to driver unit 12, in which case biopsy device 10 is made to be entirely disposable. Primary housing 16 is connected to drive housing 18, for example, by permanent connection, e.g., adhesive, weld, etc. Alternatively, drive housing 18 and biopsy probe assembly 14 may be removably mounted to primary housing 16, such that drive housing 18 and biopsy probe assembly 14 by the formed as a disposable unit separable from primary housing 16.

Drive housing 18 contains a ratchet drive mechanism 20 having a plurality of control actuators 22 (e.g., buttons and sliders), and with the plurality of control actuators 22 being accessible external to drive housing 18. Ratchet drive mechanism 20 is configured to operate biopsy probe assembly 14 to sever and receive one or more tissue samples from a patient's body. Ratchet drive mechanism 20 and the plurality of control actuators 22 are described in greater detail below.

Figure 2:
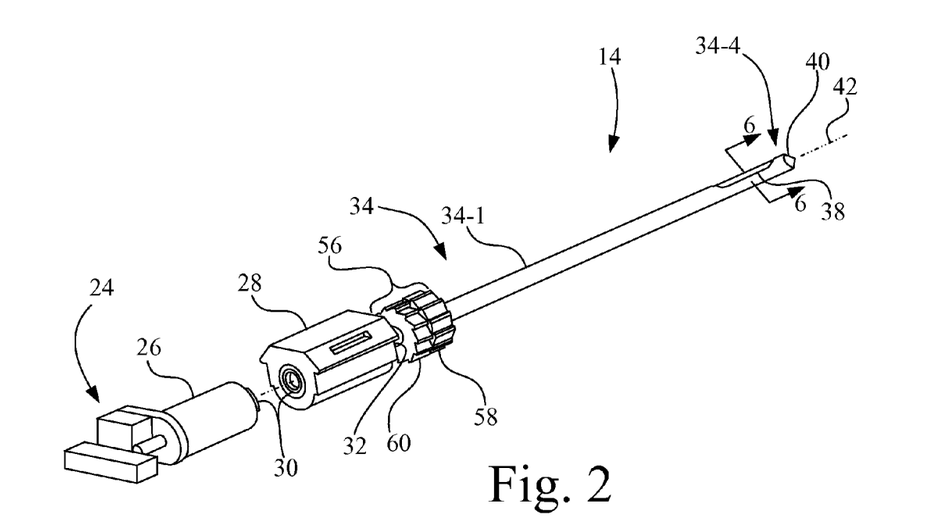
FIG. 2 shows a vacuum source and a tissue sample receptacle, and a gear unit of a ratchet drive mechanism, contained in the driver unit of the biopsy device of FIG. 1, with the tissue sample receptacle being coupled in fluid communication with the probe assembly and decoupled from the vacuum source.
Figure 3A:
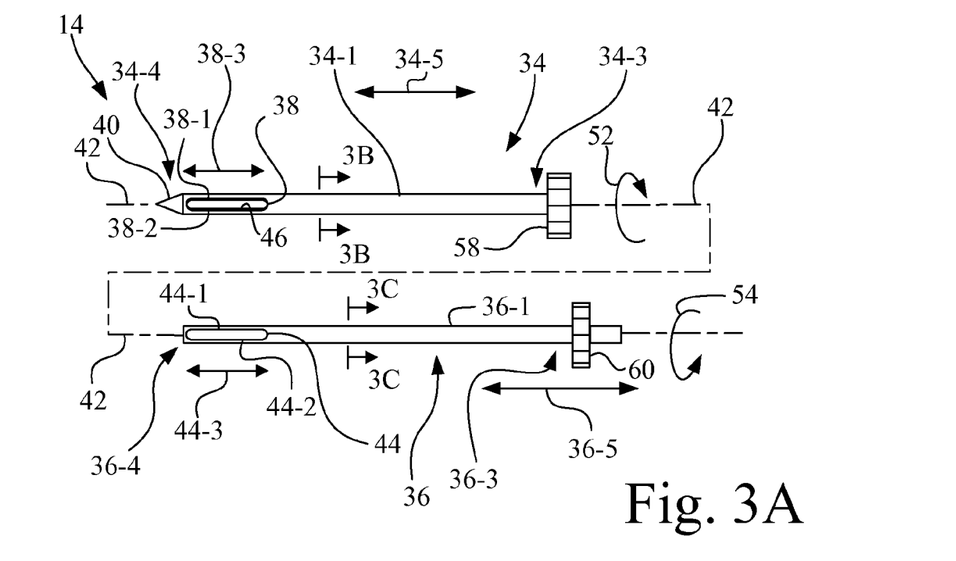
FIG. 3A is an exploded view of the probe assembly of FIG. 1, and including two gears of the gear unit of FIG. 2.
Figure 3B:
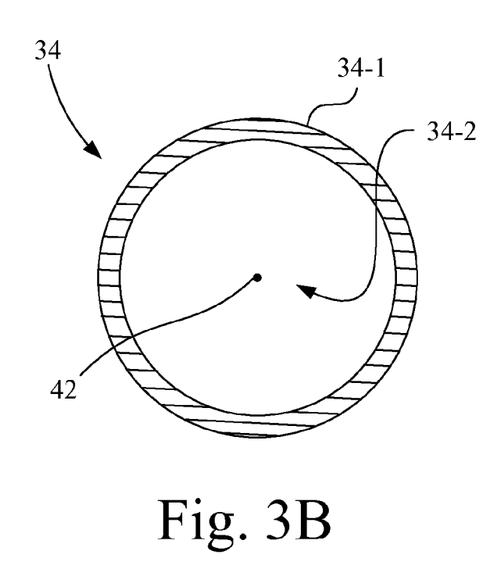
FIG. 3B is a cross-section view of the outer cannula of FIG. 3A taken along line 3B-3B.
Figure 3C:
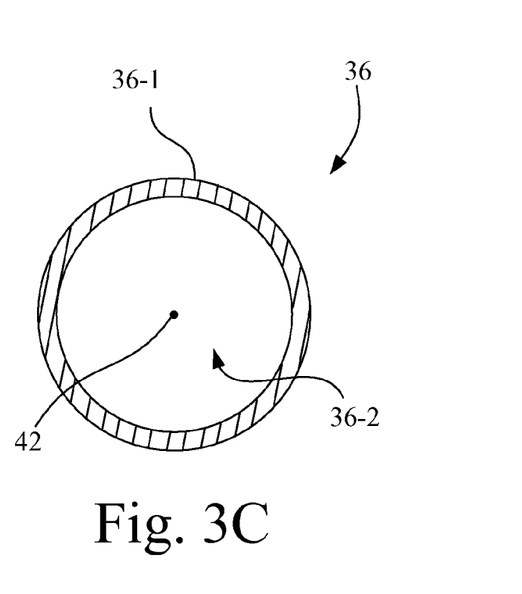
FIG. 3C is a cross-section view of the inner cannula of FIG. 3A taken along line 3C-3C.

Referring also to FIG. 2, primary housing 16 contains a power unit 24, a vacuum source 26, and a tissue sample receptacle 28. Power unit 24 includes a rechargeable battery and control circuitry to power and control vacuum source 26. Vacuum source 26 may be, for example, a driven vacuum pump, such as for example a battery/motor assisted diaphragm pump or gear driven syringe-type pump. Alternatively, power unit 24 may be replaced by an on-board gas supply to drive vacuum source 26.

Vacuum source 26 is coupled in fluid communication with tissue sample receptacle 28 via a fluid coupling 30. Fluid coupling 30 may be, for example, in the form of a mating seals arrangement or a conduit/seal arrangement. Tissue sample receptacle 28 is coupled in fluid communication with biopsy probe assembly 14 by a fluid coupling 32. Fluid coupling 32 may be, for example, in the form of a conduit/seal arrangement or mating seals arrangement.

Accordingly, negative pressure generated by vacuum source 26 is communicated to biopsy probe assembly 14 via tissue sample receptacle 28. Each tissue sample harvested by biopsy probe assembly 14 is transported by the vacuum generated by vacuum source 26 through biopsy probe assembly 14 to tissue sample receptacle 28. Tissue sample receptacle 28 may include, for example, a mesh basket (not shown) to collect the harvested tissue samples. The mesh basket and/or the collected tissue samples may be accessed through a door 16-1 of primary housing 16.

Referring also to FIGS. 3A-3C, 4, 5, and 6, biopsy probe assembly 14 includes an outer cannula 34 and an inner cannula 36.

Outer cannula 34 has a first side wall 34-1 defining a first lumen 34-2. Outer cannula 34 has a first proximal end 34-3, a first distal end 34-4, and a first aperture 38 extending through first side wall 34-1 to the first lumen 34-2 at a location proximal to first distal end 34-4. A needle tip 40 is located at first distal end 34-4 of outer cannula 34. A longitudinal axis 42 of biopsy probe assembly 14 passes centrally through first lumen 34-2 of outer cannula 34 parallel to a longitudinal extent 34-5 of outer cannula 34.

Inner cannula 36 is disposed co-axially with outer cannula 34 with respect to longitudinal axis 42. Inner cannula 36 has a second side wall 36-1 defining a second lumen 36-2. Inner cannula 36 has a second proximal end 36-3, a second distal end 36-4, and a second aperture 44 extending through second side wall 36-1 to second lumen 36-2 at a location proximal to second distal end 36-4. Longitudinal axis 42 of biopsy probe assembly 14 passes centrally through second lumen 36-2 of inner cannula 36 parallel to a longitudinal extent 36-5 of inner cannula 36.

Vacuum source 26 is in fluid communication with inner cannula 36, and may establish a continuous or intermittent negative pressure in second lumen 36-2 of inner cannula 36.

In the present embodiment as shown in FIGS. 2-6, first aperture 38 has a longitudinal edge 38-1 spaced apart from a longitudinal edge 38-2, with a longitudinal extent 38-3 of first aperture 38 being parallel to longitudinal axis 42. Second aperture 44 has a longitudinal edge 44-1 spaced apart from a longitudinal edge 44-2, with a longitudinal extent 44-3 of second aperture 44 being parallel to longitudinal axis 42. At least one of first aperture 38 of outer cannula 34 and second aperture 44 of inner cannula 36 has a cutting edge 46 that is sharpened to razor sharpness. For example, cutting edge 46 may be formed on one or more of longitudinal edges 38-1, 38-2, 44-1 and 44-2. Also, for example, the one or more of longitudinal edges 38-1, 38-2, 44-1 and 44-2 having cutting edge 46 may have an elliptical shape so that cutting edge 46 is correspondingly elliptical to aid in severing tissue.

For purposes of the discussion that follow, there is defined a first rotational direction 52 and a second rotational direction 54. From the perspective of driver unit 12 toward biopsy probe assembly 14, first rotational direction 52 is in a clockwise direction around longitudinal axis 42 and second rotational direction 54 is in a counterclockwise direction around longitudinal axis 42.

Ratchet drive mechanism 20 of driver unit 12 is operatively configured to rotate inner cannula 36 in the first rotational direction 52, or alternatively in second rotational direction 54, to sequentially position second aperture 44 at one of a plurality of angular radial positions relative to longitudinal axis 42 during a biopsy procedure to permit the taking of biopsy samples at angular radial positions around longitudinal axis 42 without manually rotating the entirety of driver unit 12. During a cocking operation, first aperture 38 of outer cannula 34 and second aperture 44 of inner cannula 36 are rotated into radial alignment by ratchet drive mechanism 20 to form a tissue sample aperture 48 to permit the tissue 50 to be biopsied to be drawn by vacuum into the second lumen 36-2 of inner cannula 36. During a firing operation, ratchet drive mechanism 20 of driver unit 12 is operatively configured to rapidly rotate outer cannula 34 relative to inner cannula 36 in second rotational direction 54 to sever the tissue 50 drawn through tissue sample aperture 48 and into second lumen 36-2 of inner cannula 36.

Figures 4, 5, 6:
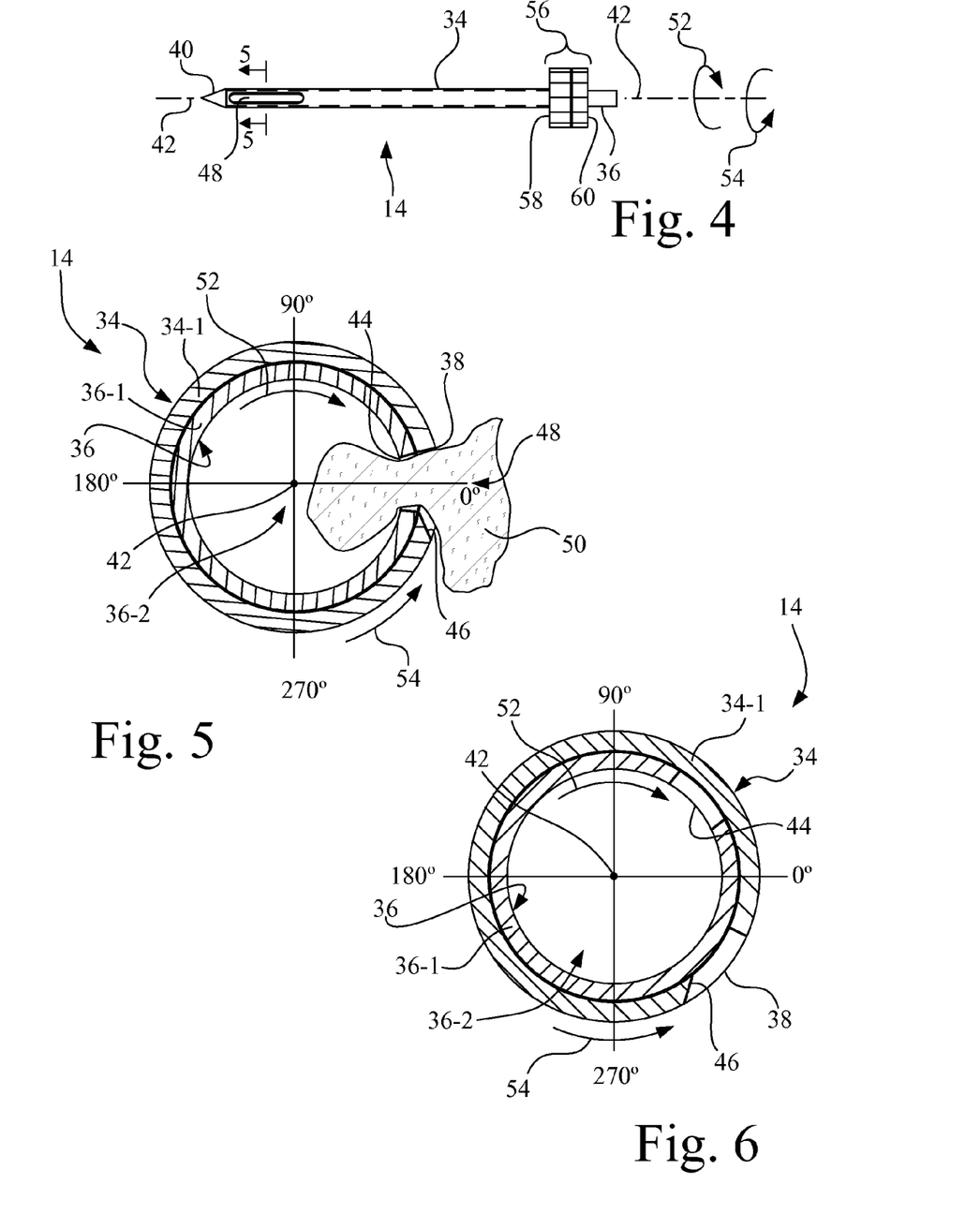
FIG. 4 is an assembled view of the probe assembly of FIG. 3A having the respective apertures of the outer cannula and inner cannula in alignment, and including the gear unit.
FIG. 5 is a cross-section view of the probe assembly of FIG. 4 taken along line 5-5, showing tissue being drawn through a tissue sample aperture.
FIG. 6 is a cross-section view of the probe assembly of FIG. 2 taken along line 6-6.

In the present embodiment, as shown in FIGS. 4 and 5, a maximum opening size of tissue sample aperture 48 is equal to the smaller of a respective opening size for each of first aperture 38 of outer cannula 34 and second aperture 44 of inner cannula 36. In some implementations, it may be desirable for first aperture 38 and second aperture 44 to be of substantially the same size.

Referring to FIGS. 2-8, ratchet drive mechanism 20 of driver unit 12 includes a gear unit 56 that includes a outer cannula gear 58, an inner cannula gear 60, and a torsion spring 62. Outer cannula gear 58 is fixedly attached to outer cannula 34 for rotation about longitudinal axis 42. Inner cannula gear 60 is fixedly attached to inner cannula 36 for rotation about longitudinal axis 42. As used herein, the term "fixedly attached" means that the respective gear and cannula are not capable of independent movement relative to each other.

Figure 7:
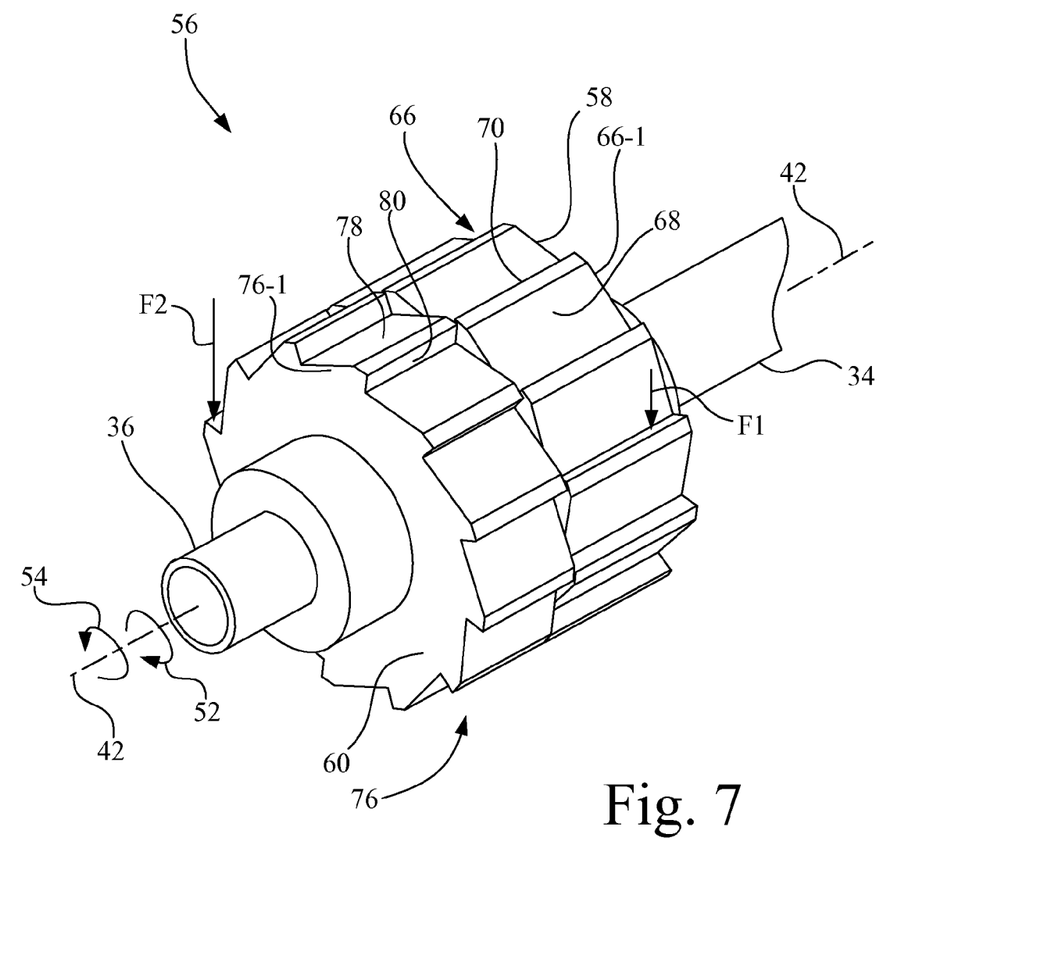
FIG. 7 is an enlarged perspective view of the gear unit of the ratchet drive mechanism of FIG. 1.
Figure 8:
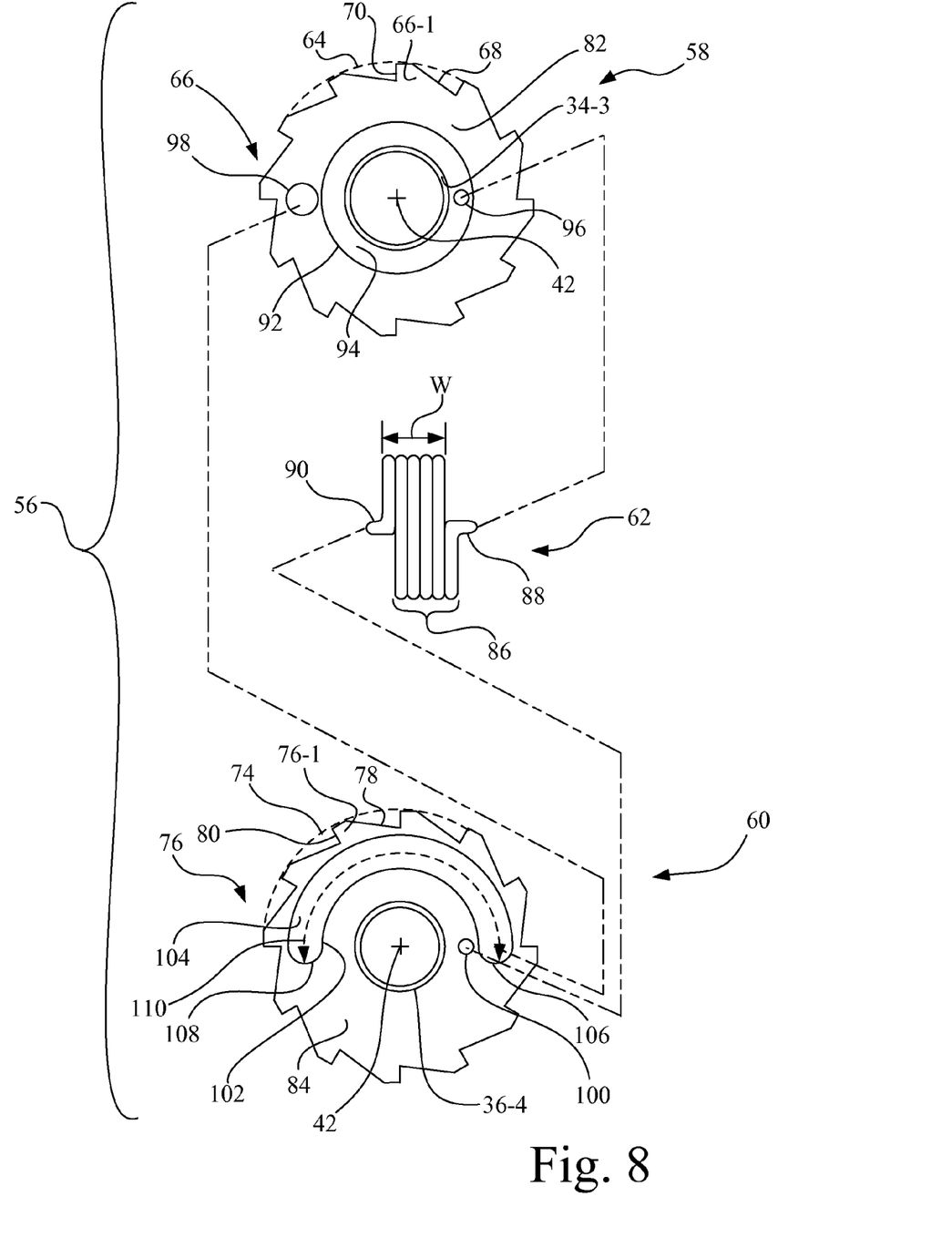
FIG. 8 is a disassembled view of the gear unit of FIG. 7, with the gears laid open to expose the respective interior features of the gears and to expose a torsion spring housed inside the gear unit.

Referring to FIGS. 7 and 8, outer cannula gear 58 is a round gear having a periphery 64 and having a plurality of ratchet teeth 66 positioned around periphery 64. Each of the plurality of ratchet teeth 66 relative to all other of the plurality of ratchet teeth 66 is uniform but asymmetrical in configuration. As best shown in FIG. 8, in the present embodiment, there are twelve identical asymmetrical ratchet teeth, with ratchet tooth 66-1 being representative of a common configuration of each of the plurality of ratchet teeth 66. Ratchet tooth 66-1 has a minor slope (bisecting periphery 64 at an acute angle, e.g., in a range of 15-45 degrees) on an outer surface 68 and a major slope (bisecting periphery 64 at an angle equal to or greater than a right angle, e.g., ≥90 degrees) on a drive surface 70. Accordingly, outer cannula gear 58 is configured to be externally driven by an external force F1 acting on drive surface 70 of each of the plurality of ratchet teeth 66. As such, outer cannula gear 58 is oriented on outer cannula 34 so as to rotate outer cannula 34 in first rotational direction 52 when acted on by the external force F1.

Inner cannula gear 60 is a round gear having a periphery 74 and having a plurality of ratchet teeth 76 positioned around periphery 74. Each of the plurality of ratchet teeth 76 relative to all other of the plurality of ratchet teeth 76 is uniform but asymmetrical in configuration. As best shown in FIG. 8, in the present embodiment, there are twelve identical asymmetrical ratchet teeth, with ratchet tooth 76-1 being representative of a common configuration of each of the plurality of ratchet teeth 76. Ratchet tooth 76-1 has a minor slope (bisecting periphery 74 at an acute angle, e.g., in a range of 15-45 degrees) on an outer surface 78 and a major slope (bisecting periphery 74 at an angle equal to or greater than a right angle, e.g., >90 degrees) on a drive surface 80. Accordingly, inner cannula gear 60 is configured to be externally driven by an external force F2 acting on drive surface 80 of each of the plurality of ratchet teeth 76. As such, inner cannula gear 60 is oriented on inner cannula 36 so as to rotate inner cannula 36 in the second rotational direction 54 when acted on by the external force F2. Also, as such, within gear unit 56, the asymmetrical orientation of the plurality of ratchet teeth 76 of inner cannula gear 60 is opposite to the asymmetrical orientation of the plurality of ratchet teeth 66 of outer cannula gear 58.

FIG. 8 shows gear unit 56 separated into the individual components, to wit: outer cannula gear 58, inner cannula gear 60, and a torsion spring 62. In FIG. 8, outer cannula gear 58 is being viewed in a direction from first proximal end 34-3 to first distal end 34-4 of outer cannula 34 (see FIG. 3A), and inner cannula gear 60 is being viewed in a direction from second distal end 36-4 toward second proximal end 36-3 of inner cannula 36 (see FIG. 3A), so as to expose the mating gear side surfaces, i.e., surface 82 of outer cannula gear 58 and surface 84 of inner cannula gear 60.

Torsion spring 62 is configured in the present embodiment as a coil spring having a plurality of coils 86 having a width W formed from a continuous length of wire having opposing end portions 88 and 90. Energy may be stored in torsion spring 62 by rotating one of, or both of, end portion 88 and end portion 90 relative to the other around longitudinal axis 42, to in effect tighten (wind) the plurality of coils 86.

Outer cannula gear 58 includes a spring recess 92 having a depth at a recessed surface 94 sufficient to receive the width W of torsion spring 62. In recessed surface 94 there is located a hole 96 for receiving end portion 88 of torsion spring 62. A pin 98, e.g., a cylindrical pin, projects outwardly from surface 82 of outer cannula gear 58 external to spring recess 92.

Inner cannula gear 60 includes a hole 100 located in surface 84 for receiving end portion 90 of torsion spring 62. Inner cannula gear 60 includes an arcuate pin recess 102 having a depth at a recessed surface 104 greater than a length of pin 98 of outer cannula gear 58. Arcuate pin recess 102 defines a first stop 106 and a second stop 108, with an angular extent 110 of arcuate pin recess 102 between first stop 106 and second stop 108 dictating the maximum relative rotational movement as between outer cannula gear 58 and inner cannula gear 60. In the present embodiment, for example the length of angular extent 110 of arcuate pin recess 102 is selected to permit a 180 degree maximum relative rotational movement as between outer cannula gear 58 and inner cannula gear 60, and in turn, as between outer cannula 34 and inner cannula 36.

When gear unit 56 is assembled, as shown in FIG. 7, torsion spring 62 exerts a slight rotational biasing force to bias pin 98 at first stop 106 of arcuate pin recess 102, as illustrated in FIG. 8. As such, outer cannula gear 58, and in turn outer cannula 34, is prevented from further rotational movement in rotational direction 54 relative to inner cannula gear 60, and in turn outer cannula 36. However, for example, when outer cannula gear 58 is acted upon by external force F1, outer cannula gear 58, and in turn outer cannula 34, is permitted to rotate in rotational direction 52 relative to inner cannula gear 60, and in turn outer cannula 36, up to the maximum extend permitted by the angular extent 110 of arcuate pin recess 102 in reaching second stop 108, so as to wind torsion spring 62 thereby storing a rotational energy in torsion spring 62 which, when released, drives outer cannula 34 rotationally in rotational direction 54 to effect tissue severing.

Figure 9:
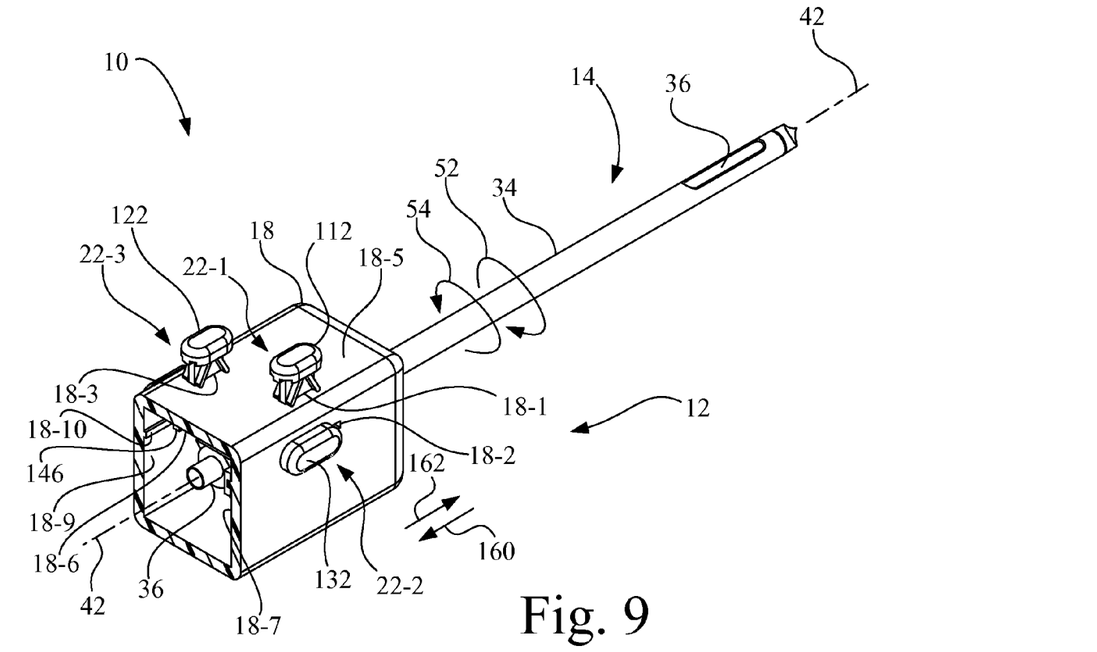
FIG. 9 is a right perspective view of the driver unit and biopsy probe assembly of FIG. 1, with the primary housing removed to expose the interior of the drive housing that mounts the ratchet drive mechanism.
Figure 10:
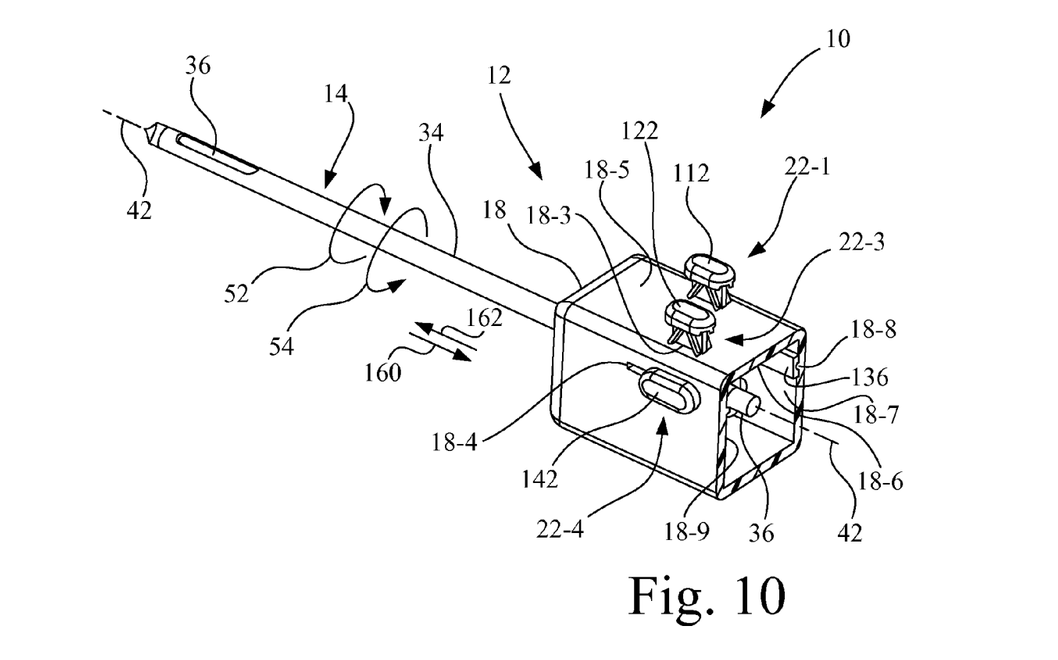
FIG. 10 is a left perspective view of the driver unit and biopsy probe assembly of FIG. 1, with the primary housing removed to expose the interior of the drive housing that mounts the ratchet drive mechanism.
Figure 11:
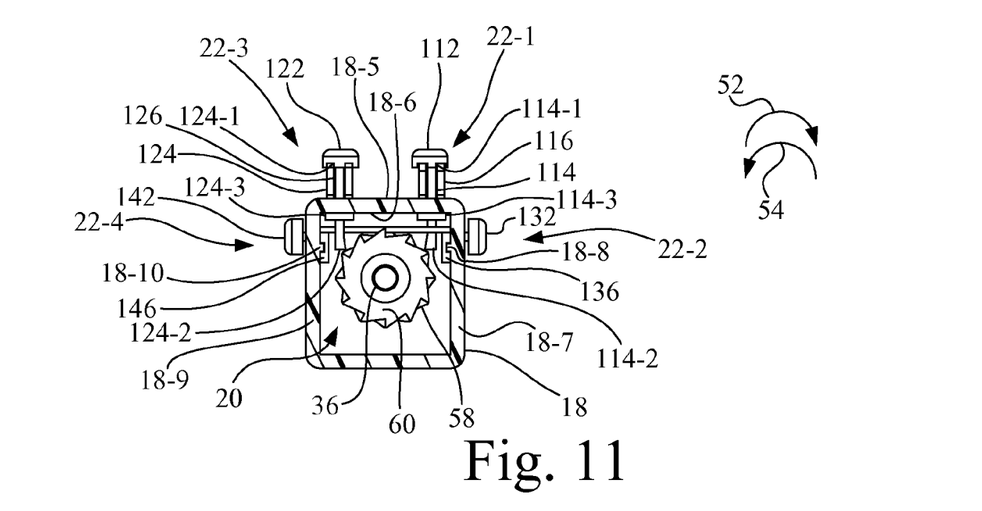
FIG. 11 is a proximal end view of the driver unit and biopsy probe assembly of FIG. 1, with the primary housing removed to expose the interior of the drive housing that mounts the ratchet drive mechanism.

Referring also to FIGS. 9-15, the plurality of control actuators 22 include an outer cannula advance actuator 22-1, an inner cannula slide actuator 22-2, an inner cannula advance actuator 22-3 and an outer cannula slide actuator 22-4. As shown in FIGS. 9 and 10, for example, outer cannula advance actuator 22-1, inner cannula slide actuator 22-2, inner cannula advance actuator 22-3 and outer cannula slide actuator 22-4 is movably mounted to drive housing 18.

Drive housing 18 includes corresponding actuator slots to respectively receive the plurality control actuators 22, namely actuator slot 18-1, actuator slot 18-2, actuator slot 18-3, and actuator slot 18-4 for respectively receiving outer cannula advance actuator 22-1, inner cannula slide actuator 22-2, inner cannula advance actuator 22-3 and outer cannula slide actuator 22-4. Drive housing 18 includes a side wall 18-7 having an inwardly facing guide rail 18-8, and includes a side wall 18-9 having an inwardly facing guide rail 18-10. Each of guide rail 18-8 and guide rail 18-10 extends substantially parallel to longitudinal axis 42.

Outer cannula advance actuator 22-1 is configured as a pushbutton having a head 112 and a shaft 114. A proximal end 114-1 of shaft is connected to head 112, and a distal end 114-2 of shaft 114 forms a free end to engage a drive surface 70 of one of the plurality of ratchet teeth 66 of outer cannula gear 58. A stop 114-3 is connected to shaft 114 at a location between proximal end 114-1 and distal end 114-2. Extending downwardly from head 112 is a spring 116, e.g., a pair of cantilever springs. Shaft 114 extends through actuator slot 18-1 of drive housing 18, with head 112 being located external to drive housing 18 and with stop 114-3 and distal end 114-2 being located internal to drive housing 18. Spring 116 is interposed between head 112 and an external surface 18-5 of drive housing 18 to bias stop 114-3 into engagement with an internal surface 18-6 of drive housing 18, thus defining a home position for outer cannula advance actuator 22-1.

Thus, spring 116 biases head 112 outwardly away from external surface 18-5 of drive housing 18. When a user applies a counterforce to head 112, spring 116 is compressed as head 112 is depressed toward external surface 18-5 and distal end 114-2 of shaft 114 engages a drive surface 70 of one of the plurality of ratchet teeth 66 of outer cannula gear 58 to incrementally rotate outer cannula gear 58, and in turn rotate outer cannula 34, around longitudinal axis 42. When the counterforce applied to head 112 is released, spring 116 returns outer cannula advance actuator 22-1 to its home position.

Inner cannula advance actuator 22-3 is configured as a pushbutton having a head 122 and a shaft 124. A proximal end 124-1 of shaft is connected to head 122, and a distal end 124-2 of shaft 124 forms a free end to engage a drive surface 80 of one of the plurality of ratchet teeth 76 of inner cannula gear 60. A stop 124-3 is connected to shaft 124 at a location between proximal end 124-1 and distal end 124-2. Extending downwardly from head 122 is a spring 126, e.g., a pair of cantilever springs. Shaft 124 extends through actuator slot 18-3 of drive housing 18, with head 122 being located external to drive housing 18 and with stop 124-3 and distal end 124-2 being located internal to drive housing 18. Spring 126 is interposed between head 122 and external surface 18-5 of drive housing 18 to bias stop 124-3 into engagement with an internal surface 18-6 of drive housing 18, thus defining a home position for inner cannula advance actuator 22-3.

Thus, spring 126 biases head 122 outwardly away from external surface 18-5 of drive housing 18. When a user applies a counterforce to head 122, spring 126 is compressed as head 122 is depressed toward external surface 18-5 and distal end 124-2 of shaft 124 engages a drive surface 80 of one of the plurality of ratchet teeth 76 of inner cannula gear 60 to incrementally rotate inner cannula gear 60, and in turn rotate inner cannula 36, around longitudinal axis 42. When the counterforce applied to head 122 is released, spring 126 returns inner cannula advance actuator 22-3 to its home position.

Inner cannula slide actuator 22-2 is configured as a slide button having a head 132, a shaft 134, an elongate guide body 136, and a cantilever pawl 138. Elongate guide body 136 includes a proximal end portion 136-1, a distal end portion 136-2, and a guide channel 136-3. Cantilever pawl 138 includes a proximal end 138-1 and a distal end 138-2. Shaft 134 extends outwardly from proximal end portion 136-1 of elongate guide body 136, and is interposed between head 132 and elongate guide body 136. Cantilever pawl 138 extends inwardly from distal end portion 136-2 in a direction from proximal end 138-1 and distal end 138-2, with distal end 138-2 forming a free end to engage a drive surface 80 of one of the plurality of ratchet teeth 76 of inner cannula gear 60.

Inner cannula slide actuator 22-2 is slidably mounted to drive housing 18 by guide channel 136-3, which slidably engages guide rail 18-8 of side wall 18-7 of drive housing 18.

By applying a force to head 132 in direction 160, inner cannula slide actuator 22-2 is slid along actuator slot 18-2 and guide rail 18-8 to disengage distal end 138-2 of cantilever pawl 138 from inner cannula gear 60. As such, inner cannula gear 60, and in turn inner cannula 36 are permitted to rotate in either of rotational direction 52 and rotational direction 54.

By applying a force to head 132 in direction 162, inner cannula slide actuator 22-2 is slid along actuator slot 18-2 and guide rail 18-8 to engage distal end 138-2 of cantilever pawl 138 with inner cannula gear 60. When distal end 138-2 of cantilever pawl 138 is engaged with one of the plurality of ratchet teeth 76 of inner cannula gear 60, rotation of inner cannula gear 60, and in turn inner cannula 36, is prevented in rotational direction 52. However, due to flexure along the length of cantilever pawl 138 toward distal end 138-2 relative to elongate guide body 136, rotation of inner cannula gear 60, and in turn inner cannula 36, is permitted in rotational direction 54, with a clicking sound being generated each time distal end 138-2 of cantilever pawl 138 drops off one tooth to an adjacent tooth of the plurality of ratchet teeth 76 of inner cannula gear 60.

Outer cannula slide actuator 22-4 is configured as a slide button having a head 142, a shaft 144, an elongate guide body 146, and a cantilever pawl 148. Elongate guide body 146 includes a proximal end portion 146-1, a distal end portion 146-2, and a guide channel 146-3. Cantilever pawl 148 includes a proximal end 148-1 and a distal end 148-2. Shaft 144 extends outwardly from proximal end portion 146-1 of elongate guide body 146, and is interposed between head 142 and elongate guide body 146. Cantilever pawl 148 extends inwardly from distal end portion 146-2 in a direction from proximal end 148-1 and distal end 148-2, with distal end 148-2 forming a free end to engage a drive surface 80 of one of the plurality of ratchet teeth 76 of outer cannula gear 58.

Outer cannula slide actuator 22-4 is slidably mounted to drive housing 18 by guide channel 146-3, which slidably engages guide rail 18-10 of side wall 18-9 of drive housing 18.

By applying a force to head 142 in direction 162, outer cannula slide actuator 22-4 is slid along actuator slot 18-4 and guide rail 18-10 to disengage distal end 148-2 of cantilever pawl 148 from outer cannula gear 58. As such, outer cannula gear 58, and in turn outer cannula 34, is permitted to rotate in either of rotational direction 52 and rotational direction 54.

By applying a force to head 142 in direction 160, outer cannula slide actuator 22-4 is slid along actuator slot 18-4 and guide rail 18-10 to engage distal end 148-2 of cantilever pawl 148 with outer cannula gear 58. When distal end 148-2 of cantilever pawl 148 is engaged with one the plurality of ratchet teeth 66 of outer cannula gear 58, rotation of outer cannula gear 58, and in turn outer cannula 34, is prevented in rotational direction 54. However, due to flexure along the length of cantilever pawl 148 toward distal end 148-2 relative to elongate guide body 146, rotation of outer cannula gear 58, and in turn outer cannula 34, is permitted in rotational direction 52, with a clicking sound being generated each time distal end 148-2 of cantilever pawl 148 drops off one tooth to an adjacent tooth of the plurality of ratchet teeth 66 of outer cannula gear 58.

The operation of ratchet drive mechanism 20 in performing a biopsy procedure will now be described with specific reference to FIGS. 2, 5, and 12-15.

Figure 12:
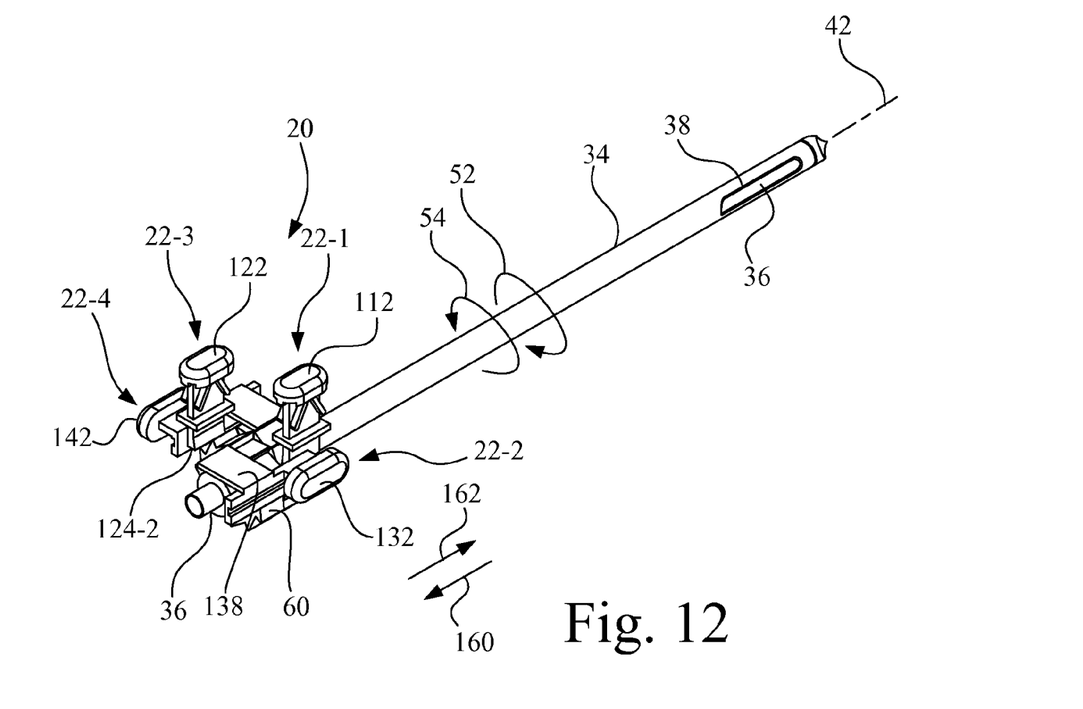
FIG. 12 is a perspective view of the ratchet drive mechanism and biopsy probe assembly of FIG. 9, with the drive housing removed.
Figure 13:
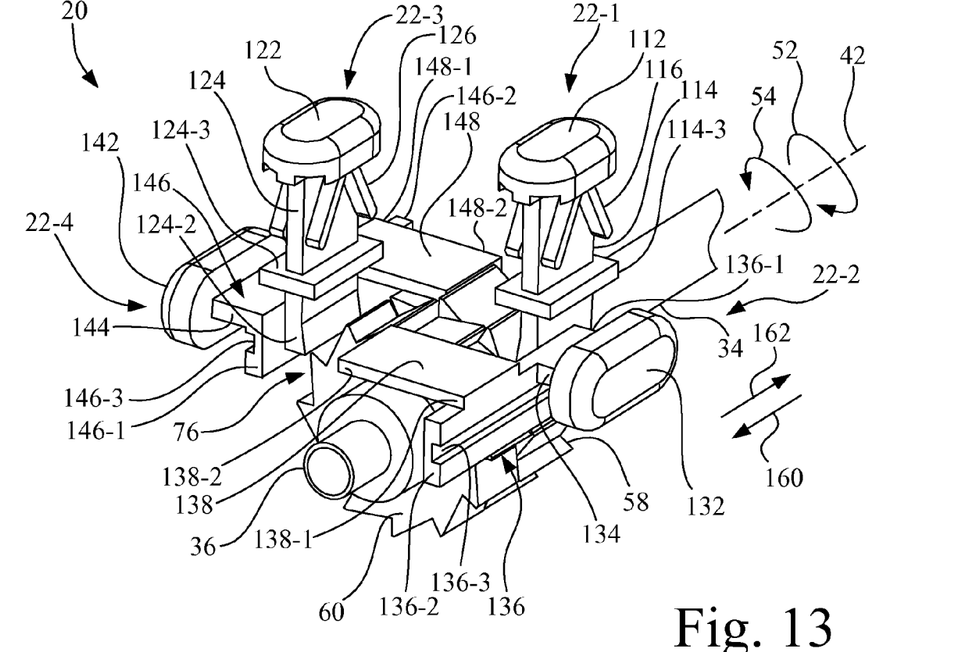
FIG. 13 is an enlarged perspective view of the ratchet drive mechanism of FIG. 12.
Figure 14:
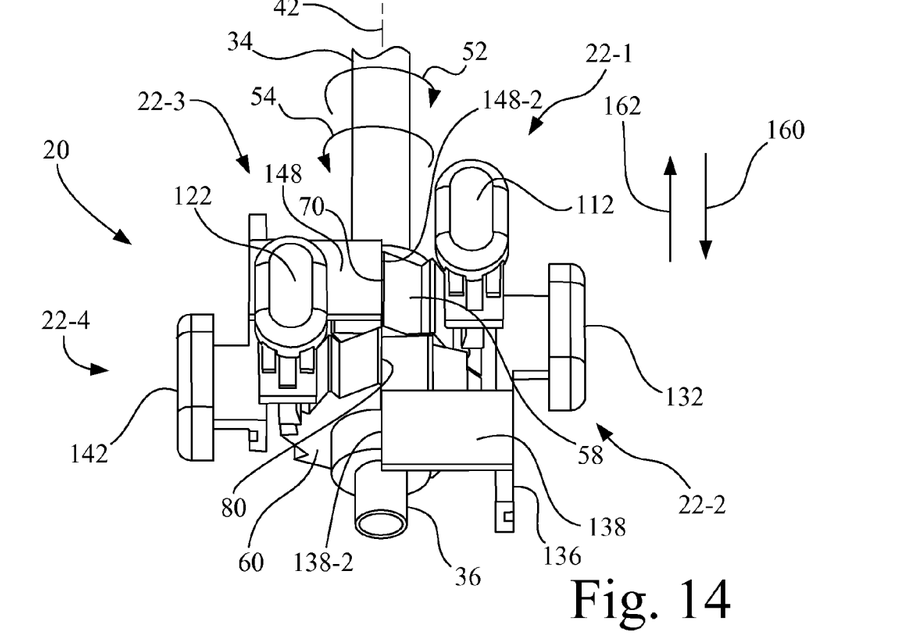
FIG. 14 is an enlarged top view of the ratchet drive mechanism of FIG. 12.

FIGS. 12, 13 and 14 illustrate a start position of inner cannula slide actuator 22-2 and outer cannula slide actuator 22-4, with inner cannula slide actuator 22-2 being disengaged from inner cannula gear 60 and outer cannula slide actuator 22-4 being engaged with outer cannula slide actuator 22-4. More specifically, in the start position, both of inner cannula slide actuator 22-2 and outer cannula slide actuator 22-4 have been slid in direction 160 to disengage distal end 138-2 of cantilever pawl 138 of inner cannula slide actuator 22-2 from inner cannula gear 60 and to engage distal end 148-2 of cantilever pawl 148 of outer cannula slide actuator 22-4 with outer cannula gear 58.

Outer cannula advance actuator 22-1 is then depressed to rotate outer cannula 34, and in turn rotate inner cannula 36 due to the coupling between outer cannula gear 58 and inner cannula gear 60 via torsion spring 62. Thus, with each depression of outer cannula slide actuator 22-4, both of outer cannula gear 58 and inner cannula gear 60 will be rotated by 30 degrees in rotational direction 52 in a clocking manner to position first aperture 38 of outer cannula 34 at the desired angular position for taking a tissue sample.

Once first aperture 38 of outer cannula 34 is at the desired angular position (e.g., the 3:00 o'clock position as illustrated in FIG. 12, also represented as the 0 degree position illustrated in FIG. 5), inner cannula slide actuator 22-2 is slid in direction 162 so that distal end 138-2 of cantilever pawl 138 is engaged with inner cannula gear 60 to preventing rotation of inner cannula gear 60 in rotational direction 52. Then inner cannula advance actuator 22-3 is pushed (depressed) a number of times (maximum of six in the present embodiment) to preload (e.g., wind) torsion spring 62, thus performing the cocking operation. With each depression of inner cannula advance actuator 22-3, inner cannula gear 60 will be rotated by 30 degrees in rotational direction 54 (up to 180 degrees) in a clocking manner, while outer cannula slide actuator 22-4 prevents rotation of outer cannula gear 58, and in turn outer cannula 34, in rotational direction 54. At the conclusion of the cocking operation, pin 98 of outer cannula gear 58 will be engaged with second stop 108 of arcuate pin recess 102 of inner cannula gear 60 to prevent further relative rotation, with second aperture 44 of inner cannula 36 having been brought into alignment with first aperture 38 of outer cannula 34 to form tissue sample aperture 48. At this time, the cocking operation is complete.

The vacuum source 26 may be actuated (before, during, or after the cocking operation) to establish a negative pressure in the second lumen 36-2 (see FIG. 5) of inner cannula 36 to thereby pull tissue 50 through the formed tissue sample aperture 48 and into the second lumen 36-2 of inner cannula 36. The negative pressure in second lumen 36-2 of inner cannula 36 is maintained during the firing (cutting) operation.

Figure 15:
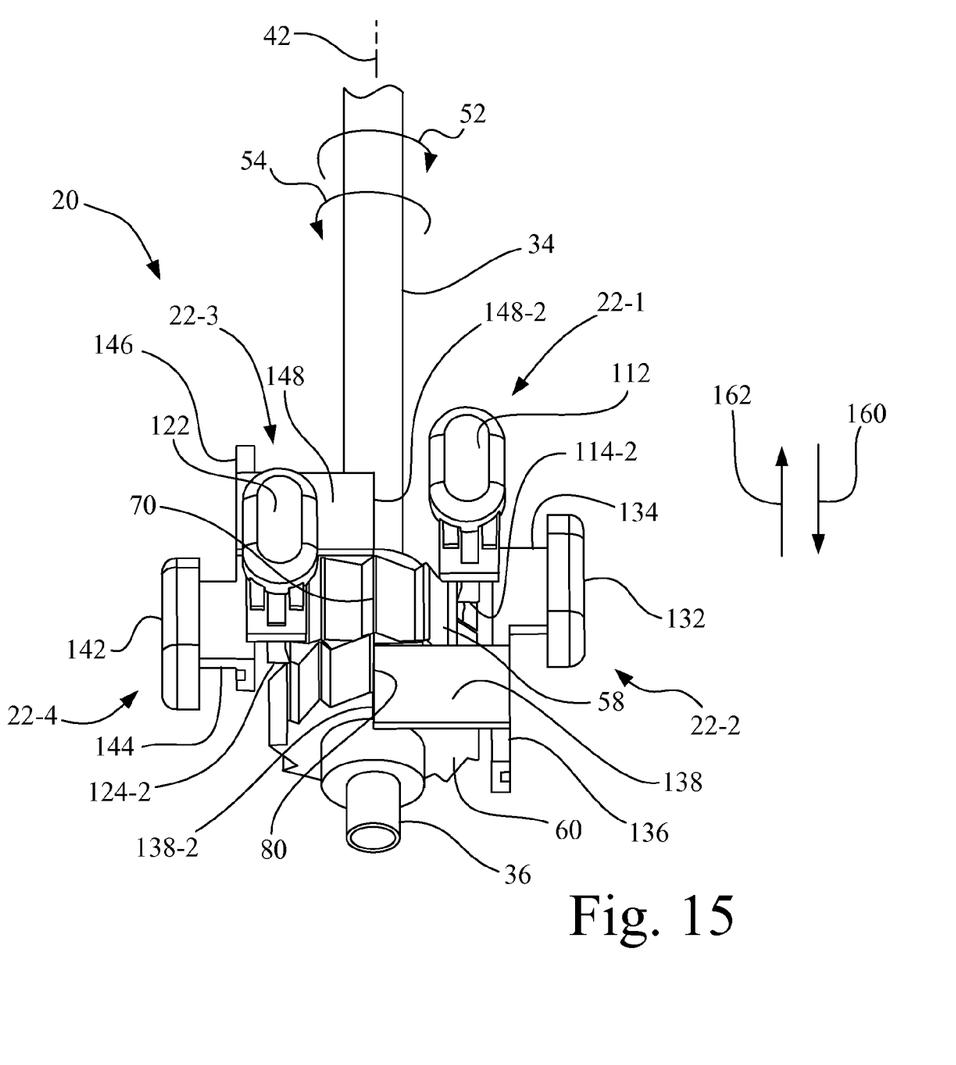
FIG. 15 is an enlarged top view of the ratchet drive mechanism corresponding generally to FIG. 14, but with the outer cannula slide actuator positioned in the firing position.

To perform the firing (cutting) operation, as illustrated in FIG. 15, outer cannula slide actuator 22-4 is slid in direction 162 to disengage distal end 148-2 of cantilever pawl 148 from outer cannula gear 58 to release the preload of torsion spring 62, which results in a rapid rotation of outer cannula 34 in rotational direction 54 relative to the stationary inner cannula 36, so as to sever the tissue 50 in second lumen 36-2 of inner cannula 36. In the present embodiment, the maximum relative rotation of outer cannula 34 with respect to inner cannula 36 is 180 degrees due to the angular extent 110 of arcuate pin recess 102 of inner cannula gear 60. Inner cannula 36 is held stationary by the continued engagement of distal end 138-2 of cantilever pawl 138 of inner cannula slide actuator 22-2 with inner cannula gear 60. The rotational velocity of outer cannula 34 relative to inner cannula 36 is defined, for example, at least in part by the spring stiffness of torsion spring 62 and the maximum relative rotation of outer cannula 34 with respect to inner cannula 36 as defined by angular extent 110 of arcuate pin recess 102.

Once tissue 50 is severed, the severed tissue sample is transported by the negative pressure in second lumen 36-2 through inner cannula 36 to tissue sample receptacle 28 (see FIG. 2).

If additional tissue samples are desired, both of inner cannula slide actuator 22-2 and outer cannula slide actuator 22-4 are slid in direction 160 to disengage distal end 138-2 of cantilever pawl 138 from inner cannula gear 60 and to reengage distal end 148-2 of cantilever pawl 148 with outer cannula gear 58, so as to return the components of ratchet drive mechanism 20 to the start position illustrated in FIG. 12, and the process described above is repeated.

Due to the configuration of ratchet drive mechanism 20, it is possible to perform the cocking operation using an alternative process. For example, in this implementation initially inner cannula slide actuator 22-2 is engaged with inner cannula gear 60 and outer cannula slide actuator 22-4 is disengaged from outer cannula gear 58. Then, inner cannula advance actuator 22-3 is pushed (depressed) a number of times to position second aperture 44 of inner cannula 36 at the desired the desired angular position (e.g., the 3:00 o'clock position as illustrated in FIG. 12, also represented as the 0 degree position illustrated in FIG. 5). Once the desired angular position is achieved, outer cannula 34 is locked from further rotation in rotational direction 54 by sliding outer cannula slide actuator 22-4 into engagement with outer cannula gear 58.

Outer cannula advance actuator 22-1 is then pushed (depressed) a number of times (maximum of six in the present embodiment) to preload (e.g., wind) torsion spring 62, thus performing the cocking operation. With each depression of outer cannula advance actuator 22-1, outer cannula 34 will be rotated by 30 degrees in rotational direction 52 (up to 180 degrees), while inner cannula slide actuator 22-2 prevents rotation of inner cannula gear 60, and in turn inner cannula 36, in rotational direction 52. At the conclusion of the cocking operation, pin 98 of outer cannula gear 58 will be engaged with second stop 108 of arcuate pin recess 102 of inner cannula gear 60 to prevent further relative rotation, with first aperture 38 of outer cannula 34 having been brought into alignment with second aperture 44 of inner cannula 36 to form tissue sample aperture 48. At this time, the cocking operation is complete.

The establishing of vacuum and the firing operation may then be performed as previously described.

While this invention has been described with respect to embodiments of the invention, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A biopsy device, comprising:
a first cannula having a first side wall defining a first lumen, said first cannula having a first proximal end and a first distal end, said first cannula having a first aperture extending through said first side wall to said first lumen proximal to said first distal end, said first cannula having a longitudinal axis;
a second cannula having a second side wall defining a second lumen, said second cannula having a second proximal end and a second distal end, said second cannula having a second aperture extending through said second side wall to said second lumen proximal to said second distal end, said second cannula being disposed co-axially with said first cannula, at least one of said first aperture and said second aperture having a cutting edge; and
a driver unit having a ratchet drive mechanism operatively coupled to said first cannula and said second cannula, said ratchet drive mechanism including:
a first gear fixedly attached to said first cannula;
a second gear fixedly attached to said second cannula;
a torsion spring located between said first gear and said second gear, said torsion spring having a first end portion and a second end portion, said first end portion being connected to said first gear and said second end portion being connected to said second gear, said ratchet drive mechanism being configured such that said torsion spring stores energy which when released drivably rotates one of said first gear and said second gear relative to the other of said first gear and said second gear,
wherein said first cannula is an outer cannula having a needle tip located at said first distal end and second cannula is an inner cannula positioned in said first lumen of said outer cannula, said ratchet drive mechanism being configured to wind said torsion spring to store said energy during a cocking operation and configured to release said torsion spring during a firing operation to drivably rotate said first gear to rotate said outer cannula relative to said inner cannula;
an outer cannula advance actuator configured to rotate said first gear in discrete rotational increments in a first rotational direction;
an inner cannula advance actuator configured to rotate said second gear in discrete rotational increments in a second rotational direction opposite to said first rotational direction;
an outer cannula slide actuator having a first cantilever pawl, said outer cannula slide actuator being configured to selectively engage said first gear, wherein when said first cantilever pawl is engaged with said first gear, said first gear and said outer cannula are prevented from rotation in said second rotational direction; and
an inner cannula slide actuator having a second cantilever pawl, said inner cannula slide actuator being configured to selectively engage said second gear, wherein when said second cantilever pawl is engaged with said second gear, said second gear and said inner cannula are prevented from rotation in said first rotational direction.

2. The biopsy device of claim 1, wherein in order to store said energy in said torsion spring, said outer cannula slide actuator is positioned to prevent rotation of said first gear in said second rotational direction, said inner cannula slide actuator is positioned to prevent said second gear from rotation in said first rotational direction, and said inner cannula advance actuator is depressed at least one time to rotate said second gear in said second rotational direction to wind said torsion spring.

3. The biopsy device of claim 1, wherein in order to store said energy in said torsion spring, said outer cannula slide actuator is positioned to prevent rotation of said first gear in said second rotational direction, said inner cannula slide actuator is positioned to prevent said second gear from rotation in said first rotational direction, and said outer cannula advance actuator is depressed at least one time to rotate said first gear in said first rotational direction to wind said torsion spring.

4. A biopsy device, comprising:
an outer cannula having a first side wall defining a first lumen, said outer cannula having a first aperture extending through said first side wall to said first lumen, said outer cannula having a longitudinal axis;
an inner cannula having a second side wall defining a second lumen, said inner cannula having a second aperture extending through said second side wall to said second lumen, said inner cannula being disposed co-axially with said outer cannula in said first lumen, at least one of said first aperture and said second aperture having a cutting edge; and
a ratchet drive mechanism operatively coupled to said outer cannula and said inner cannula, said ratchet drive mechanism including:
a first gear fixedly attached to said outer cannula;
a second gear fixedly attached to said inner cannula;
a torsion spring located between said first gear and said second gear, said torsion spring having a first end portion and a second end portion, said first end portion being connected to said first gear and said second end portion being connected to said second gear;

an outer cannula advance actuator configured to rotate said first gear in discrete rotational increments in a first rotational direction;

an inner cannula advance actuator configured to rotate said second gear in discrete rotational increments in a second rotational direction opposite to said first rotational direction;

an outer cannula slide actuator having a first cantilever pawl, said outer cannula slide actuator being configured to selectively engage said first gear, wherein when said first cantilever pawl is engaged with said first gear, said first gear and said outer cannula are prevented from rotation in said second rotational direction; and an inner cannula slide actuator having a second cantilever pawl, said inner cannula slide actuator being configured to selectively engage said second gear, wherein when said second cantilever pawl is engaged with said second gear, said second gear and said inner cannula are prevented from rotation in said first rotational direction.

5. The biopsy device of claim 4, wherein in order to store energy in said torsion spring, said outer cannula slide actuator is positioned to prevent rotation of said first gear in said second rotational direction, said inner cannula slide actuator is positioned to prevent said second gear from rotation in said first rotational direction, and said inner cannula advance actuator is depressed at least one time to rotate said second gear in said second rotational direction to wind said torsion spring, and said energy stored in said torsion spring is released to drivably rotate said first gear relative to said second gear by repositioning said outer cannula slide actuator to permit rotation of said first gear in said second rotational direction.

6. The biopsy device of claim 5, wherein a rotational velocity of outer cannula relative to said inner cannula is defined, at least in part, by a spring stiffness of said torsion spring and a maximum relative rotation of said outer cannula with respect to said inner cannula.

7. The biopsy device of claim 4, wherein in order to store said energy in said torsion spring, said outer cannula slide actuator is positioned to prevent rotation of said first gear in said second rotational direction, said inner cannula slide actuator is positioned to prevent said second gear from rotation in said first rotational direction, and said outer cannula advance actuator is depressed at least one time to rotate said first gear in said first rotational direction to wind said torsion spring, and said energy stored in said torsion spring is released to drivably rotate said first gear relative to said second gear by repositioning said outer cannula slide actuator to permit rotation of said first gear in said second rotational direction.

8. The biopsy device of claim 7, wherein a rotational velocity of outer cannula relative to said inner cannula is defined, at least in part, by a spring stiffness of said torsion spring and a maximum relative rotation of said outer cannula with respect to said inner cannula.

9. The biopsy device of claim 4, wherein said first gear has a first feature and said second gear has a second feature, said first feature being engaged with said second feature to limit an extent of relative rotation between said outer cannula and said inner cannula.

10. The biopsy device of claim 9, wherein said first feature is a pin extending outwardly from a first side surface of said first gear, and said second feature is an arcuate pin recess located in a second side surface of said second gear, said pin being positioned in said arcuate pin recess, and wherein a maximum relative rotation of said outer cannula with respect to inner cannula is defined by an angular extent of said arcuate pin recess.

11. The biopsy device of claim 10, wherein a rotational velocity of outer cannula relative to said inner cannula is defined, at least in part, by a spring stiffness of said torsion spring and said maximum relative rotation of said outer cannula with respect to said inner cannula.

12. The biopsy device of claim 10, wherein said first gear has a spring recess located between said first gear and said second gear, said spring recess being configured to receive said torsion spring.

* * * * *